US012782296B2

(12) United States Patent
Alqahtani et al.

(10) Patent No.: US 12,782,296 B2
(45) Date of Patent: Nov. 3, 2026

(54) IN-SITU IMAGING AND CHARACTERIZATION OF HYDRAULIC FRACTURE DEVELOPMENT

(71) Applicant: Saudi Arabian Oil Company, Dhahran (SA)

(72) Inventors: Hassan Alqahtani, Dammam (SA); Moath I. Gazlan, Khobar (SA); Naif J. Alqahtani, Dammam (SA); Murtadha J. AlTammar, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 317 days.

(21) Appl. No.: 18/442,642

(22) Filed: Feb. 15, 2024

(65) Prior Publication Data

US 2025/0264420 A1 Aug. 21, 2025

(51) Int. Cl.

| | |
|---|---|
| ***G01N 23/046*** | (2018.01) |
| ***G01N 1/44*** | (2006.01) |
| ***G01N 3/06*** | (2006.01) |
| ***G01N 3/12*** | (2006.01) |
| ***G01N 23/083*** | (2018.01) |
| ***G01N 33/24*** | (2006.01) |

(52) U.S. Cl.
CPC ............ *G01N 23/046* (2013.01); *G01N 1/44* (2013.01); *G01N 3/06* (2013.01); *G01N 3/12* (2013.01); *G01N 23/083* (2013.01); *G01N 33/24* (2013.01)

(58) Field of Classification Search
CPC .......... G01N 23/046; G01N 1/44; G01N 3/06; G01N 3/12; G01N 23/083; G01N 33/24; G01N 33/241; G01N 2203/0256; G01N 2223/616; G01N 23/18
See application file for complete search history.

(56) References Cited

U.S. PATENT DOCUMENTS

| | | | |
|---|---|---|---|
| 4,867,243 | A | 9/1989 | Garner |
| 9,348,056 | B2 | 5/2016 | Fredrich et al. |
| 9,587,649 | B2 | 3/2017 | Oehring |

(Continued)

FOREIGN PATENT DOCUMENTS

| | | | | |
|---|---|---|---|---|
| CN | 110687140 A | * | 1/2020 | ............... G01N 3/12 |
| WO | WO 2009149362 | | 12/2009 | |
| WO | WO 2017106724 | | 6/2017 | |

OTHER PUBLICATIONS

English machine translation of Zhang et al, CN-110687140-A, Jan. 14, 2020 (Year: 2020).*

(Continued)

*Primary Examiner* — David Z Huang
(74) *Attorney, Agent, or Firm* — Dinsmore & Shohl LLP

(57) ABSTRACT

To perform in-situ imaging and characterization of hydraulic fracture development, a triaxial test assembly is configured to evaluate a core sample obtained from a hydrocarbon formation. The triaxial test assembly is positioned within a Computer Tomography (CT) imaging system. While the triaxial test assembly is positioned within the CT imaging system, a core sample is connected to the triaxial test assembly. The triaxial test assembly is operated to evaluate the core sample. The CT imaging system is operated while evaluating the core sample by operating the test assembly. Properties of the core sample are determined using results of operating the triaxial test assembly and of operating the CT imaging system.

7 Claims, 3 Drawing Sheets

(56) References Cited

U.S. PATENT DOCUMENTS

| | | | | |
|---|---|---|---|---|
| 10,458,334 | B2 | 10/2019 | Davis | |
| 10,571,605 | B2 | 2/2020 | Crawford et al. | |
| 10,741,158 | B1 | 8/2020 | Aune | |
| 10,926,227 | B2 | 2/2021 | Cha et al. | |
| 11,422,285 | B2 | 8/2022 | Wang et al. | |
| 11,619,127 | B1 | 4/2023 | AlTammar et al. | |
| 11,660,595 | B2 | 5/2023 | Wang et al. | |
| 2010/0230093 | A1 | 9/2010 | Knudsen | |
| 2016/0208592 | A1 | 7/2016 | Oehring | |
| 2017/0003263 | A1* | 1/2017 | Huang | G01N 33/24 |
| 2017/0066959 | A1 | 3/2017 | Hull et al. | |
| 2019/0068026 | A1 | 2/2019 | Davis | |
| 2020/0072044 | A1 | 3/2020 | Zhang | |
| 2021/0286096 | A1 | 9/2021 | Jin | |
| 2021/0293127 | A1 | 9/2021 | Donderici | |

OTHER PUBLICATIONS

Alheshibri et al., "A History of Nanobubbles," Langmuir, Nov. 2016, 32(43):11086-111000, 15 pages.

alibaba.com [online], "API 6A wellhead flange Adapter Spool Casing Spool," available on or before 2021, retrieved on Oct. 19, 2021, retrieved from URL <https://www.alibaba.com/product-detail/API-6A-wellhead-flange-Adapter-Spool_62086814814.html>, 5 pages.

Bésuelle et al., "Experimental characterisation of the localisation phenomenon inside a Vosges sandstone in a triaxial cell," Int J Rock Mech Min Sci, Sep. 12, 2000;37:1223-1237, 15 pages.

Cnudde et al., "High-resolution X-ray computed tomography in geosciences: a review of the current technology and applications," Earth Science Reviews, Aug. 2013;123, 17 pages.

Crandall et al., "CT scanning and flow measurements of shale fractures after multiple shearing events," Int J Rock Mech Min Science, Dec. 2017;100:177-187, 11 pages.

Hlidek et al., "Cost Effective Monitoring and Visualization System Used for Real-Time Monitoring of Downhole Operations from the Wellhead," SPE-181688-MS, Society of Petroleum Engineers, 2016, 9 pages.

Hlidek, "Proven hydraulic fracturing field applications for real-time visualization and monitoring system," SPE-187126-MS, Society of Petroleum Engineers, Oct. 2017, 6 pages.

Hou et al., "Fracture Initiation and Propagation In A Deep Shale Gas Reservoir Subject To An Alternating-Fluid-Injection Hydraulic-Fracturing Treatment," SPE-195571-PA, Society of Petroleum Engineers, SPE Journal, May 14, 2019, 24(04):1839-1855, 18 pages.

Hull et al., "Chemomechanical effects of oxidizer-CO2 systems upon hydraulically fractured unconventional source rock," The Canadian Journal of Chemical Engineering, Jul. 26, 2021, 100(6):1417-1426, 26 pages.

Hull et al., "Oxidative Kerogen Degradation: A Potential Approach to Hydraulic Fracturing In Unconventionals," Energy & Fuels, May 1, 2019, 33(6):4758-4766, 9 pages.

insulationexpress.co.uk [online], "Soundproofing Walls," available on or before Oct. 30, 2020, via Internet Archive: Wayback Machine URL <http://web.archive.org/web/20201030172854/https://www.insulationexpress.co.uk/guides/acoustic-insulation/how-to-soundproof-a-wall/>, retrieved on Oct. 19, 2021, URL <https://www.insulationexpress.co.uk/blog/soundproofing-walls.html>, 7 pages.

Money, "Oklahoma eyes earthquakes tied to well completions," The Oklahoman, Dec. 24, 2017, 2 pages.

Pirzada et al., "$CO_2$ sorption induced damage in coals in unconfined and confined stress states: a micrometer to core scale investigation," Int J Coal Geol Oct. 1, 2018, 198,167-176, 10 pages.

Rahim, "Hydraulic Fracturing—2020," Journal of Petroleum Technology, cover page, Mar. 2020, 6 pages.

Ren et al., "Materials for Microfluidic Chip Fabrication," Accounts of Chemical Research, Jun. 2013, 46(11):2396-2406, 11 pages.

Rodoplu et al., "Evolution of Limited Entry Multi Stage Stimulation Completion Technology for Improved Acid Stimulation in Tight Carbonate Reservoirs," SPE-192256-MS, Society of Petroleum Engineers, 2018, 18 pages.

Roshan et al., "Microstructural Effects On Mechanical Properties Of Shaly Sandstone," J Geotech Geoenviron Engineering, Feb. 2018, 144(2): 06017019, 8 pages.

seismos.com [online], "Real-time Acoustic MWF™ Solutions (Measurements While Fracing)," available on or before 2020, retrieved on Oct. 19, 2021, retrieved from URL https://www.seismos.com/, 5 pages.

siemens-energy.com [online], "Siemens Energy Electrical and Mechanical Solutions (SEAM) for Pressure Pumping and Mobile Oilfield Applications," available on or before Sep. 19, 2020, via Internet Archive: Wayback Machine URL <http://web.archive.org/web/20200919133308/https://www.siemens-energy.com/global/en/offerings/industrial-applications/oil-gas/upstream/unconventional-resources/seam.html>, retrieved on Oct. 19, 2021, URL https://www.siemens-energy.com/global/en/offerings/industrial-applications/oil-gas/upstream/unconventional-resources/seam.html, 7 pages.

Song et al., "Chip-off-the-old-rock: The study of reservoir-relevant geological processes with real-rock micromodels," Lab Chip, Sep. 2014, 14, 4382-4390, 11 pages.

soundproofingstore.co.uk [online], "ReductoClip™ System," available on or before 2020, retrieved on Oct. 19, 2021, retrieved from URL https://www.soundproofingstore.co.uk/reducto-clip-system, 17 pages.

soundproofingstore.co.uk [online], Ian Baker, "What is the best sound proof acoustic insulation?," Oct. 4, 2019, retrieved on Feb. 24, 2022, retrieved from URL <https://www.soundproofingstore.co.uk/soundproofing-insulation>, 14 pages.

Takano et al., "Localised deformation in a wide-grained sand under triaxial compression revealed by X-ray tomography and digital image correlation," Soils Found Aug. 2015;55(4)::906-915, 10 pages.

Tanaka et al., "Concentration and Dilution of Ultrafine Bubbles in Water," Colloids Interfaces, 2020, 4(4):50, 15 pages.

Zhang et al. "Laboratory Evaluation of a Low Ph And Low Polymer Concentration Ziconium CMHPG Gel System For Hydraulic Fracturing," Energy & Fuels, Sep. 26, 2019, 33, 9720-9735, 16 pages.

Zhao et al., "Rotary shear experiments under X-ray micro-computed tomography," Rev Sci Instrum, Jan. 26, 2017;88(1)::015110, 10 pages.

Zheng et al., "A Nanoparticle Assisted $CO_2$ Huff-N-Puff Field Test in the Eagle Ford Shale," SPE-200375-MS, In SPE Improved Oil Recovery Conference—Virtual, Aug. 30, 2020, 17 pages.

Glatz et al., "An experimental platform for triaxial high-pressure/high-temperature testing of rocks using computed tomography," Apr. 2018, 89(4):045101, 11 pages.

Zhuang et al., "Laboratory hydraulic fracturing experiments on crystalline rock for geothermal purposes," Earth-Science Reviews, Mar. 2021, 216(2):103580, 34 pages.

International Search Report and Written Opinion in International Appln. No. PCT/US2025/015746, mailed May 15, 2025, 12 pages.

* cited by examiner

IN-SITU IMAGING AND CHARACTERIZATION OF HYDRAULIC FRACTURE DEVELOPMENT

TECHNICAL FIELD

This disclosure relates to wellbore characterization, and specifically to evaluating a wellbore core, for example, for hydraulic fracturing development.

BACKGROUND

Unconventional hydrocarbon resources include source rocks with low permeability. Hydraulic fracturing stimulation is a technique to enhance production in such hydrocarbon resources. The fracturing forms conductive and efficient multi-stages of hydraulic fractures in the source rock that enhances extraction and flow rates through those stages. The increased flow channels in the hydraulically opened fractures depends on factors including overreach extended horizontal well length, the number of stages completed, the cluster spacings, fluid systems treatment volumes and the fluid system additives.

Stimulated Reservoir Volume (SRV) creates hydraulic fractures surrounded by induced microfractures around the main hydraulic fractures by using high-rate, slickwater fracturing of unconventional formations, e.g., shale formations. Chemical additives, e.g., nanoparticles/carbon dioxide ($CO_2$) and concentrated fluid oxidizers (kerogen/organic matter treatment) can enhance productivity in hydraulically fractured source rock formations.

One technique to characterize and evaluate the development of hydraulic fractures in unconventional hydrocarbon resources is to study fluid flow through a core sample obtained from the source rock under different flow conditions. A triaxial test is an example of such a technique. In a triaxial test, a core sample is subjected to high pressure across multiple axes.

SUMMARY

This specification describes technologies relating to in-situ imaging and characterization of hydraulic fracture development.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure describes in situ CT high resolution imaging and physical characterization of fractures in unconventional rock formations, both natural and induced, including microfractures. In the context of this disclosure, in situ means capturing CT images of unconventional rock formations, e.g., of core samples obtained from such formations, while the core samples are being evaluated. As described below, evaluating core samples can include applying different levels of stresses (ranging from no stress to stress that induces fracture in the core sample) to the core samples, and capturing one or more CT images μthe different levels of stresses. CT images captured at no stress levels can reveal naturally present fractures in the core samples. CT images captured at other stress levels can reveal the propagation of fractures (both micro- and macro-fractures) in the core sample with increasing stress levels. Additional core sample evaluations using the techniques described here are described below.

Implementing the techniques described here can provide an experimental setup that can provide high resolution images useful in the characterization of core samples. For example, 6 millimeter (mm) core samples can be evaluated to capture fracture images with a resolution of 1 micrometer (μm) per voxel or less. The core samples can be evaluated using a triaxial test assembly. Triaxial loading and CT imaging can be implemented while subjecting the core samples to a range of temperatures ranging from room temperature to as high as 90° C. Images obtained using the CT imaging system can be combined with measurements obtained from the triaxial test assembly to evaluate gas flow through the core sample. Loading and imaging can be implemented while subjecting the core samples to a range of pressures (or both pressures and temperatures). The inducement and development of fractures (both micro- and macro-fractures) over time can be evaluated under the applied conditions. The techniques described here can also be used to characterize fracture geometry such as aperture and surface roughness. The techniques can also be used to compute and model fracture conductivity under the different stress levels (including pressure and temperature levels) that mimic real reservoir environments.

Figure 1:
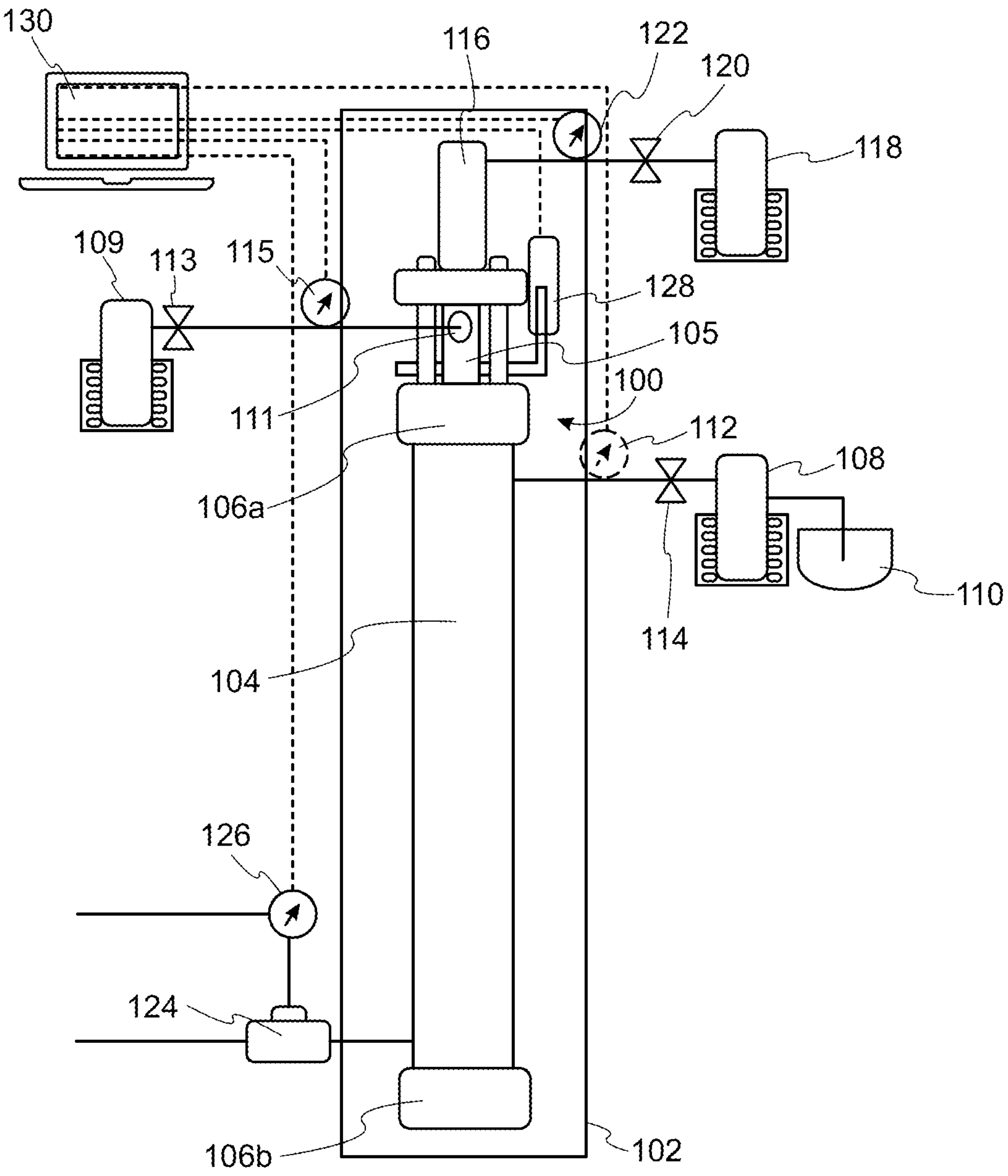
FIG. 1 is a schematic diagram of a triaxial test assembly positioned within a Computer Tomography (CT) imaging system.

FIG. 1 is a schematic diagram of a triaxial test assembly 100 positioned within a Computer Tomography (CT) imaging system 102. The triaxial test assembly 100 is a core flooding system that can operate to analyze a core sample (FIG. 2) as well as fluid flow through the core sample under various and varying conditions such as pressures and temperatures. In some implementations, the triaxial test assembly 100 can also apply conditions such as vibrational frequencies, acoustic wave energy, rotation and tilting to the core sample, either alone or in combination with any of the other conditions.

The triaxial test assembly 100 includes a core holder 104, for example, a housing (such as a cylindrical housing), that can be enclosed on open ends by end plates (106*a*, 106*b*) to define an inner volume. The core sample can be inserted into the inner volume and enclosed within by the core holder 104 and the end plates 106*a*, 106*b*. In some implementations, a sleeve 105 (e.g., a rubber sleeve) can be used to hold the core sample within the inner volume of the core holder 104. Rather than applying certain conditions (e.g., pressure) directly onto the surface of the core sample, such conditions can be applied onto the sleeve 105 within which the core sample is held. A fluid (e.g., water, oil, gas, a mixture thereof) can be circulated through the inner volume of the core holder 104 to contact or saturate (or both) the core sample. In some implementations, openings/valves (not shown) can be formed in the end plates 106*a*, 106*b* to regulate the flow of the fluid through the core holder 104.

The triaxial test assembly 100 can conduct core flooding and interfacial tension contact angle tests that mimic reservoir conditions (e.g., pressure, temperature, reservoir fluids). The assembly 100 can apply a constant pressure across the end plates 106*a*, 106*b* or constant flow through the end plates 106*a*, 106*b*. Core flooding results can then be used to guide mathematical models and extract critical simulation parameters.

To perform such tests, the assembly 100 can include multiple flow control equipment. For example, a pump 108 can flow fluids through the core holder 104. The fluids can be stored in a temperature-controlled bath (or reservoir) 110. Fluid flow by the pump 108 through the core holder 104 can be regulated using the transducer 112 (e.g., a pressure transducer) and the valve 114. In some implementations, the transducer 112 can alternatively or additionally sense temperature and regulate a temperature of fluid in the bath 110 using the sensed temperature. Another pump 109 can pump fluid directly into the sleeve 105, e.g., through an opening 111. Fluid flow by the pump 109 can be regulated using a valve 113 and a pressure transducer 115. All valves used in the assembly 100 can be two-way valves that permit fluid flow in both directions. Similarly, all pumps used in the assembly 100 can drive fluid into or out of the core holder 104 or the sleeve 105. The transducers (pressure transducers, temperature transducers) used in the assembly can sense parameters (pressure, temperature) and transmit signals representing the sensed parameters to an external device. Alternatively or in addition, the transducers can measure the parameters (pressure, temperature) represented by the signals.

Examples of fluids that the pumps can flow through the core holder 104 include confining pressure fluid to apply confining pressure to the core sample or the sleeve 105 within which the core sample is placed. Examples of fluids can also include hydraulic pressure fluid to apply uniaxial pressure to the core sample, and injection fluid using which permeability or relative permeability of the core sample (and by extension, the subsurface formation) can be determined.

To apply such fluidic pressure within the core holder 104 and/or to flow fluid through the core sample, the assembly 100 can include a hydraulic ram 116. A pump 118 can flow fluid, regulated by a valve 120 and a pressure transducer 122, to drive the hydraulic ram 116. The valve 120 and the pressure transducer 122 can control flow parameters such as flow rate, applied pressure, time rate of change of pressure, etc. The system 100 also includes a back pressure regulator 124 coupled to a pressure transducer 126 that can measure pressure within the core holder 104. Based on the pressure sensed or measured by the transducer 126, the back pressure regulator 124 can regulate fluidic pressure within the core holder 104. In some implementations, the assembly 100 includes a linear variable differential transformer (LVDT) 128 that can measure a volumetric strain response of the core sample to the applied stress.

The assembly 100 can include a computer system 130 to which all components described above can be operatively connected (e.g., through wired or wireless connections or networks). The computer system 130 can include a computer-readable medium (e.g., a non-transitory computer-readable medium) storing computer instructions and one or more processors operatively connected to the computer-readable medium. The one or more processors can execute the computer instructions to perform operations described in this disclosure. The operations can include, for example, transmitting control signals to control operation of the various components. For example, the computer system 130 can transmit control signals to the various pumps to pump fluids through the core holder 104. In particular, the computer system 130 can control a rate at which the various pumps flow the fluids. To do so, the computer system 130 can receive pressure signals from the various pressure transducers and responsively control the various flow valves. In another example, the computer system 130 can transmit control signals to control a temperature of the bath 110 based, in part, on temperatures sensed by the transducer 112.

The computer system 130 can also be operatively connected to the transducers that measure flow conditions within the core holder 104 and the sleeve 105, and, from these transducers, receive signals representative of flow. The computer system 105 can also be operatively connected to the LVDT 128. The computer system 130 can process the signals representing the flow conditions and other signals received from the various components of the assembly 100 to determine information about the core sample.

In some implementations, the triaxial test assembly 100 is positioned within the CT imaging system 102. The CT imaging system 102 is an imaging system that uses a rotating X-ray tube and a row of detectors to measure X-ray attenuations within an object being imaged. The X-ray measurements taken from different angles can then be processed using a computer system (e.g., the computer system 130) using tomographic reconstruction algorithms to produce tomographic (cross-sectional) images of the object. The CT imaging system 102 can define an hollow internal region within which the triaxial test assembly 100 can be positioned without interfering with rotating mechanics and gears of the rotating stage of the CT imaging system 102. As described below, the CT imaging system 102 and the triaxial test assembly 100 can be operated simultaneously so that the CT imaging system 102 can capture images of the core sample while the triaxial test assembly 100 is operated to perform core evaluation tests described above. The computer system 130 can receive the output of the CT imaging system 102 and the triaxial test assembly 100, process the output, and simultaneously present the output on a computer monitor of the computer system 130. Such an arrangement allows, among other aspects, visualization and analysis of fracture development in the core sample.

Figure 2:
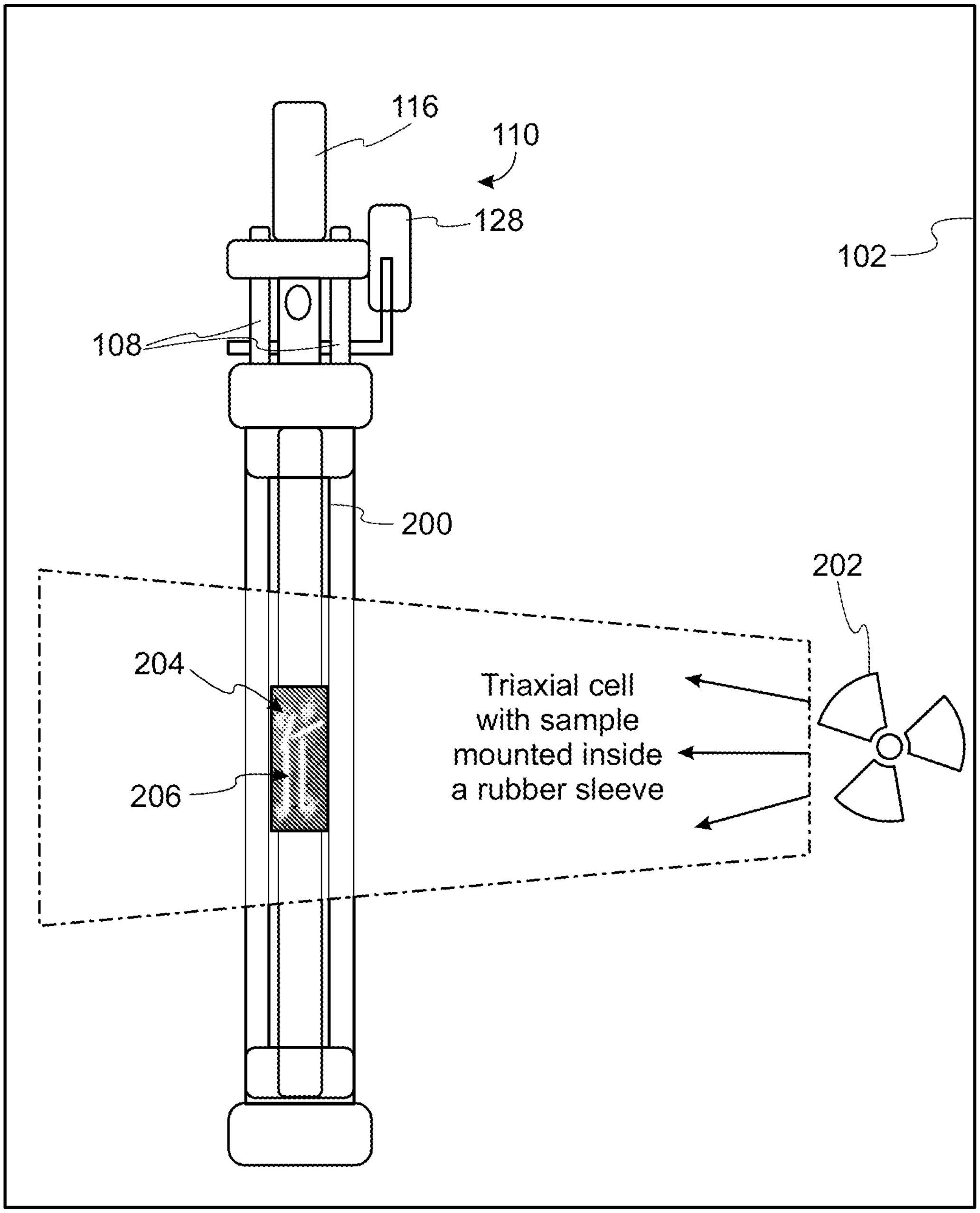
FIG. 2 is a schematic diagram of the CT imaging system capturing images of a core sample while the core sample is evaluated by the triaxial test assembly.

FIG. 2 is a schematic diagram of the CT imaging system 102 capturing images of a core sample while the core sample 200 is evaluated by the triaxial test assembly 100. As described above, the core sample 200 is obtained from a subsurface hydrocarbon formation. The combination of the triaxial test assembly 100 and the CT imaging system 102 can be used to evaluate the core sample 200, specifically to test the development of fractures in the core sample 200. Such testing can include measuring stress/strain responses in the core sample 200 while simultaneously capturing CT images of the core sample 200 in response to the application of external stresses. Examples of external stresses can include fluidic pressure applied to an external surface of the core sample 200, fluid flow through the core sample 200, application of heat to the core sample 200 or any combination of them. The stress/strain responses and the CT images can be processed by the computer system 130 (FIG. 1).

In some implementations, the core sample 200 obtained from the hydrocarbon formation is connected to the triaxial test assembly 100. For example, the core sample 200 is positioned within the core holder (FIG. 1) or within the sleeve (FIG. 1) which is then positioned within the core holder (FIG. 1). The triaxial test assembly 100 with the core sample 200 is positioned within the CT imaging system 102.

For example, the assembly 100 is positioned in the hollow space defined by the rotary X-ray tubes 202 of the CT imaging system 102. Using the triaxial test assembly 100, fluidic pressure is applied to the core sample 200. For example, the hydraulic ram 116 applies the fluidic pressure on the external surface of the core sample 200. With the core holder (FIG. 1) closed on both ends, the fluidic pressure increases over a duration of time. While the fluidic pressure is increased over the duration of time, the CT imaging system 102 is operated to capture multiple images of the core sample 200. Each image is captured at a respective time instant (e.g., one image per second or multiple images per second or a different frequency) in the duration of time. In parallel, the transducers (FIG. 1) measure stress/strain responses of the core sample 200 to the pressure applied over the duration. For example, the LVDT 128 measures strain responses of the core sample 200. The transducer measurements and the captured images can be transmitted to the computer system (FIG. 1). The computer system (FIG. 1) can process the transducer measurements and the captured images to evaluate the core sample 200. For example, using the transducer measurements and the captured images, the computer system can determine properties of the core sample such as porosity and permeability, or properties of flow through the core sample or combinations of them.

In some instances, increasing the fluidic pressure over time causes fractures to develop in the core sample 200. The fractures can be microfractures 204 (e.g., up to 10 micrometers in dimension)) or macrofractures 206 (e.g., greater than 10 micrometers in dimension). The CT imaging system 102 can capture images of the fractures, both micro- and macro-fractures. In particular, as the fluidic pressure increases over the duration of time, each fracture forms and further propagates. For each time instant in the duration, the computer system 130 can store a pressure measurement across the core sample 200, a CT image captured at that time instant, and the time instant itself. Using such information stored for multiple time instants in the duration, the computer system 130 can generate trend data that shows pressure responses and CT images associated with the pressure responses. The trend data can allow a user to determine a precise time instant at which fractures began to form in the core sample 200, how the fractures propagated over time and how the pressure responses changed with fracture formation and propagation (i.e., fracture development).

In some implementations, the CT imaging system 102 can be configured to begin taking CT images only when fracture formation in the core sample 200 is detected. For example, the computer system 130 can control the triaxial test assembly 100 to apply fluidic pressure on the core sample 200 as described above and continuously measure an increasing pressure differential across the core sample 200 in response to the applied fluidic pressure. Beyond a certain limit, the core sample 200 develops a fracture at which point a pressure differential across the core sample 200 drops. The computer system 130 can be configured to determine a reversal in the time rate of change of pressure (i.e., from increasing rate before fracture development to decreasing rate after fracture development), and responsively operate the CT imaging system 102 to begin capturing CT images while continuing to increase the applied fluidic pressure. The computer system 130 can receive and store pressure differential measurements and CT images, the combination of which can provide information about fracture development in the core sample 200 with increasing fluidic pressures.

In another example use of the system, the response of the core sample 200 to the application of temperature can be determined. For example, after positioning the triaxial test assembly 100 with the core sample 200 within the CT imaging system 102, a temperature of the core sample 200 can be increased. To do so, the computer system 130 can control the temperature of the fluid in the temperature-controlled bath (FIG. 1) and cause the pump (FIG. 1) to flow the temperature controlled fluid through the core holder (FIG. 1) or into the sleeve (FIG. 1). In this manner, the computer system 130 can increase a temperature applied to the core sample 200 over a duration of time. While the temperature is increased over the duration of time, the computer system 130 can operate the CT imaging system 102 to capture multiple images of the core sample, each captured at a respective time instant in the duration of time. In this manner, a temperature response of the core sample 200 over the duration of time can be evaluated. In some implementations, both pressure and temperature can be simultaneously applied to the core sample 200 and CT images captured as described above. The resulting combinations of fluidic pressure, temperature, triaxial stresses on the core sample in response the fluidic pressure or the temperature (or both) and images captured by the CT imaging system 102 can be recorded at each time instant across the duration of time. The recorded combinations can be made available (e.g., displayed on a monitor) to allow evaluation of the core sample 200.

Figure 3:
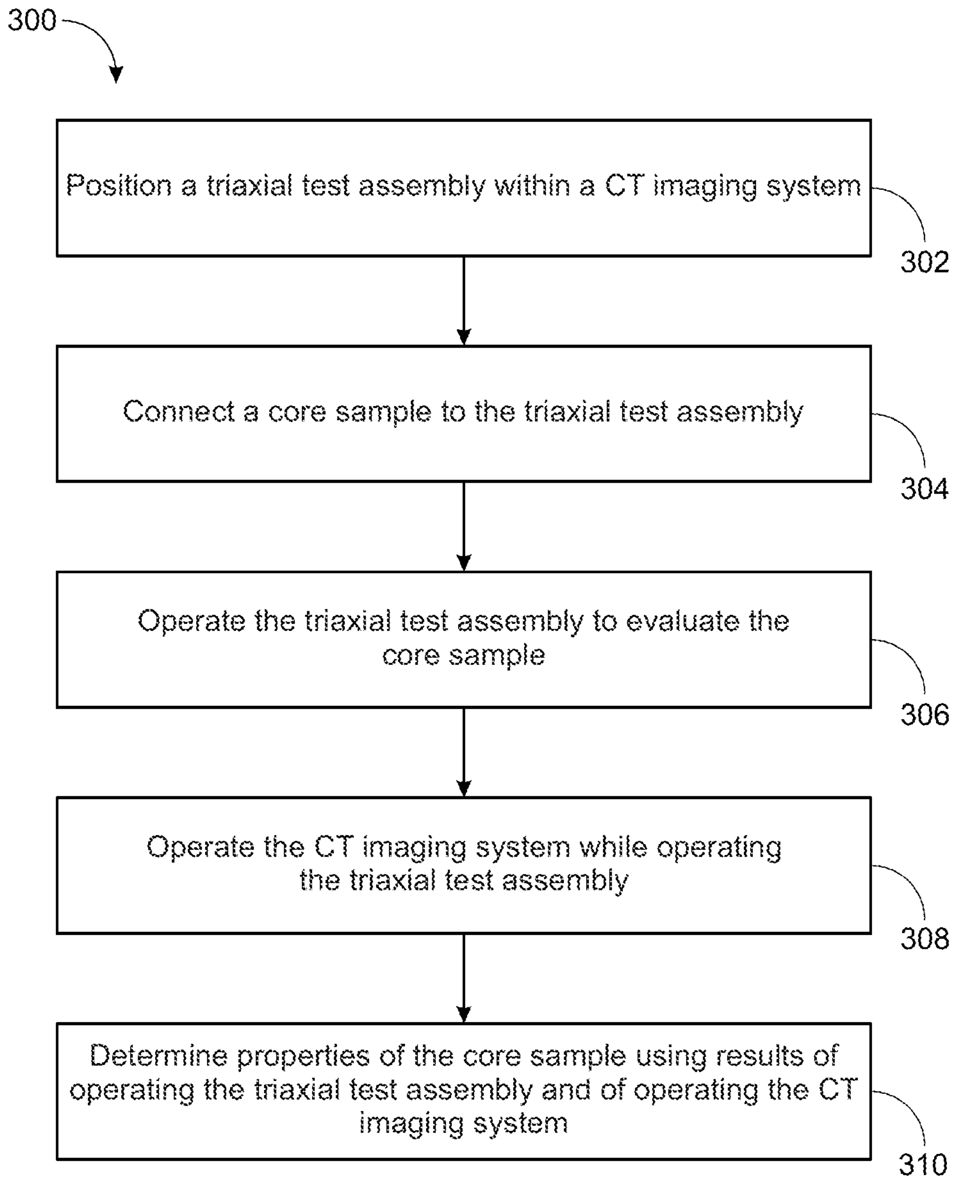
FIG. 3 is a flowchart of an example of a process of evaluating a core sample using a triaxial test assembly while capturing images of the core sample using a CT imaging system.

FIG. 3 is a flowchart of an example of a process 300 of evaluating a core sample using a triaxial test assembly (e.g., the triaxial test assembly 100) while capturing images of the core sample using a CT imaging system (e.g., the CT imaging system 102). At 302, a triaxial test assembly is positioned within a CT imaging system. At 304, a core sample is connected to the assembly. For example, the core sample is positioned within a core holder or within a sleeve which is then positioned within the core holder. At 306, the assembly is operated to evaluate the core sample. For example, the assembly evaluates the core sample by applying triaxial stresses to the core sample in the form of fluidic pressure. Alternatively or in addition, the assembly can evaluate the core sample by applying temperature to the core sample. In some instances, the core evaluation can include flowing fluid through the core sample. The fluid can include single phase fluid like gas, brine or oil. The core evaluation can include measuring responses, e.g., flow properties of the fluid, temperature response of the core sample, etc., in response to subjecting the core sample to the conditions described above. At 308, the CT imaging system can be operated to capture images of the core sample while operating the triaxial test assembly. At 310, properties of the core sample can be determined using results of operating the triaxial test assembly and of operating the CT imaging system.

The techniques described here provide an in situ X-ray transparent experimental set up that can be used to combine volumetric strain response of core samples to applied stress with visualization of such responses. The resulting information can be used to construct stress-strain curves and computer mechanical rock properties while also providing visual information about the samples. The images captured using the CT imaging system can be used to estimate, by image processing techniques such as digital rock analysis, fracture geometry, aperture and surface roughness. The techniques can also allow obtaining high resolution images of core samples as those samples are being subjected to conditions reservoir conditions in terms of triaxial stresses, pressure and temperature. The results of measurements obtained by using the experimental set up can be used to model fluid flow through fractures with high accuracy, e.g., by solving fluid flow equations (Navier-Stokes equations) on three-dimensional models of the fracture domain through numerical solution.

Examples

Certain aspects of the subject matter described here can be implemented as a method of evaluating a core sample obtained from a hydrocarbon formation. A triaxial test assembly is configured to evaluate a core sample obtained from a hydrocarbon formation. The triaxial test assembly is positioned within a Computer Tomography (CT) imaging system. While the triaxial test assembly is positioned within the CT imaging system, a core sample is connected to the triaxial test assembly. The triaxial test assembly is operated to evaluate the core sample. The CT imaging system is operated while evaluating the core sample by operating the test assembly. Properties of the core sample are determined using results of operating the triaxial test assembly and of operating the CT imaging system.

An aspect combinable with any other aspect includes the following features. To operate the CT imaging system while evaluating the core sample by operating the triaxial test assembly, images of fractures formed in the core sample are captured while evaluating the core sample by operating the triaxial test assembly.

An aspect combinable with any other aspect includes the following features. The triaxial test assembly includes a sleeve to receive the core sample. To connect the core sample to the triaxial test assembly, the core sample is positioned within the sleeve. The sleeve is positioned within the CT imaging system.

An aspect combinable with any other aspect includes the following features. To operate the triaxial test assembly, fluidic pressure is applied to the core sample positioned within the sleeve.

An aspect combinable with any other aspect includes the following features. To apply the fluidic pressure, the sleeve is flooded with a fluid that applies the fluidic pressure to a lateral surface of the core sample.

An aspect combinable with any other aspect includes the following features. The fluid is a single phase fluid.

An aspect combinable with any other aspect includes the following features. The fluid includes gas, brine or oil.

An aspect combinable with any other aspect includes the following features. Properties of the fluid are measured while applying the fluidic pressure.

An aspect combinable with any other aspect includes the following features. To capture images of fractures formed in the core sample, multiple images of fractures are captured over a period of time for which the fluidic pressure is applied to the core sample positioned within the sleeve.

An aspect combinable with any other aspect includes the following features. To operate the triaxial test assembly, heat is applied to the core sample positioned within the sleeve.

An aspect combinable with any other aspect includes the following features. To apply the heat, a temperature within the sleeve is increased at a controlled rate.

An aspect combinable with any other aspect includes the following features. To capture images of fractures formed in the core sample, multiple images of fractures are captured over a period of time for which the temperature within the sleeve is increased at the controlled rate.

An aspect combinable with any other aspect includes the following features. The results of operating the triaxial test assembly include pressure measurements in response to applying a pressure across the core sample and temperature measurements in response to applying a temperature to the core sample. The results of operating the CT imaging system include images of fractures formed in the core sample in response to applying the pressure and applying the temperature. To determine the properties of the core sample using results of operating the triaxial test assembly and of operating the CT imaging system, the pressure measurements, the temperature measurements and the images are transmitted to a computer system. The computer system processes the pressure measurements, the temperature measurements and the images of fractures.

Certain aspects of the subject matter described here can be implemented as a method. A core sample obtained from a hydrocarbon formation is connected to a triaxial test assembly. The triaxial test assembly is connected to the core sample within a CT imaging system. The triaxial test assembly applies fluidic pressure to the core sample. The fluidic pressure is increased over a duration of time. While the fluidic pressure is increased over the duration of time, the CT imaging system captures multiple images of the core sample. Each image is captured at a respective time instant in the duration of time.

An aspect combinable with any other aspect includes the following features. The fluidic pressure increased over the duration of time causes a fracture in the core sample. The CT imaging system captures an image of the fracture.

An aspect combinable with any other aspect includes the following features. A drop in the fluidic pressure across the core sample represents creation of the fracture in the core sample. An image of the core sample is captured after determining the drop in the fluidic pressure.

An aspect combinable with any other aspect includes the following features. The fluidic pressure is a first evaluation of the core sample. A second evaluation of the core sample separate from the first evaluation is performed. In the second evaluation, after positioning the triaxial test assembly connected to the core sample within the CT imaging system, a temperature of the core sample is increased. The temperature is increased over a duration of time. While the temperature is increased over the duration of time, the CT imaging system captures multiple images of the core sample. Each image is captured at a respective time instant in the duration of time.

An aspect combinable with any other aspect includes the following features. Over the duration of time, combinations of fluidic pressure, triaxial stresses on the core sample in response to the fluidic pressure and an image captured by the CT imaging system are captured at the time instant at which the fluidic pressure and the triaxial stresses are measured.

An aspect combinable with any other aspect includes the following features. The triaxial test assembly includes a sleeve to receive the core sample. To connect the core sample to the triaxial test assembly, the core sample is positioned within the sleeve. The sleeve is positioned within the CT imaging system.

An aspect combinable with any other aspect includes the following features. Based on the applied fluidic pressure and on the multiple images of the core sample, properties of the core sample are determined. The properties include a porosity of the core sample.

Thus, particular implementations of the subject matter have been described. Other implementations are within the scope of the following claims.

The invention claimed is:

1. A method of evaluating a core sample obtained from a hydrocarbon formation, the method comprising:

positioning a triaxial test assembly configured to evaluate a core sample obtained from a hydrocarbon formation within a Computer Tomography (CT) imaging system, wherein the triaxial test assembly comprises a core holder, a confining pressure pump, a core flooding pump, a hydraulic ram pump, a hydraulic ram, and a linear variable differential transformer (LVDT);

positioning a core sample in a sleeve of the core holder of the triaxial test assembly, wherein the core holder is enclosed by a first end plate and a second end plate, thereby defining an inner volume within which the sleeve is positioned;

operating the triaxial test assembly to evaluate the core sample, comprising:

operating the core flooding pump to flow a fluid into the sleeve and against the core sample, operating the hydraulic ram pump to drive the hydraulic ram against the core flood fluid and the core sample, thereby applying a uniaxial fluid pressure on the core sample, operating the confining pressure pump to flow a confining pressure fluid against an exterior of the sleeve, thereby applying a confining pressure on the core sample through the sleeve, and increasing a fluid pressure on the core sample via the core flooding pump;

measuring stress/strain responses in the core sample via the LVDT while increasing the fluid pressure on the core sample via the core flooding pump;

capturing CT images of the core sample via the CT imaging system while increasing the fluid pressure on the core sample via the core flooding pump;

transmitting the stress/strain responses and the CT images of the core sample to a computer system; and determining properties of the core sample via the computer system using the stress/strain responses and the CT images.

2. The method of claim 1, wherein capturing CT images via the CT imaging system comprises capturing images of fractures formed in the core sample.

3. The method of claim 2, wherein capturing images of fractures formed in the core sample comprises capturing a plurality of images of fractures over a period of time in which the fluid pressure on the core sample is increased via the core flooding pump.

4. The method of claim 2, wherein operating the triaxial test assembly comprises applying heat to the core sample positioned within the sleeve.

5. The method of claim 4, wherein applying heat to the core sample comprises increasing a temperature within the sleeve at a controlled rate.

6. The method of claim 5, wherein capturing images of fractures formed in the core sample comprises capturing a plurality of images of fractures over a period of time for which the temperature within the sleeve is increased at the controlled rate.

7. The method of claim 1, further comprising measuring properties of the core flooding fluid while increasing the fluid pressure on the core sample via the core flooding pump.

* * * * *